(12) United States Patent
Thynne, Jr.

(10) Patent No.: US 9,999,538 B2
(45) Date of Patent: Jun. 19, 2018

(54) OBSTRUCTIVE SLEEP APNEA AND SNORING PREVENTION DENTAL APPLIANCE

(71) Applicant: Garry Ross Thynne, Jr., Las Vegas, NV (US)

(72) Inventor: Garry Ross Thynne, Jr., Las Vegas, NV (US)

( * ) Notice: Subject to any disclaimer, the term of this patent is extended or adjusted under 35 U.S.C. 154(b) by 307 days.

(21) Appl. No.: 14/874,286

(22) Filed: Oct. 2, 2015

(65) Prior Publication Data

US 2016/0193074 A1  Jul. 7, 2016

Related U.S. Application Data

(60) Provisional application No. 62/099,284, filed on Jan. 2, 2015.

(51) Int. Cl.
*A47G 9/08* (2006.01)
*A61F 5/56* (2006.01)
*A63B 71/08* (2006.01)

(52) U.S. Cl.
CPC ............. *A61F 5/566* (2013.01); *A61F 5/56* (2013.01); *A61F 2005/563* (2013.01); *A63B 2071/086* (2013.01)

(58) Field of Classification Search
CPC ...... A61F 5/56; A61F 5/566; A61F 2005/563; A63B 71/085; A63B 2071/086; A63B 2071/088; A61C 7/08; A61C 7/36; A61M 16/0488; A61M 16/049; A61M 16/0493; A61M 16/0495

USPC ........................................................ 433/140
See application file for complete search history.

(56) References Cited

U.S. PATENT DOCUMENTS

| | | | | | |
|---|---|---|---|---|---|
| 2,521,039 | A | * | 9/1950 | Carpenter | A63B 71/085 128/861 |
| 3,217,708 | A | * | 11/1965 | Roberts | A63B 71/085 128/861 |
| 3,768,465 | A | * | 10/1973 | Helmer | A63B 71/085 128/862 |
| 4,112,936 | A | * | 9/1978 | Blachly | A61M 16/0488 128/207.14 |
| 6,109,266 | A | * | 8/2000 | Turchetti | A63B 71/085 128/861 |

(Continued)

*Primary Examiner* — Alireza Nia
*Assistant Examiner* — Rachel Berezik
(74) *Attorney, Agent, or Firm* — Plager Schack LLP

(57) ABSTRACT

Some embodiments of the present disclosure include a dental appliance for treating/preventing sleep apnea and snoring. The dental appliance may be a wedge-shaped device designed to be positioned between the lower and upper jaw, wherein the device is thicker within a front area of the mouth and thinner within a back area of the mouth. The device may include upper and lower teeth channels to accommodate the teeth and a plurality of breathing ports positioned between the upper and lower teeth channels, the breathing ports being configured to allow a user to breathe through the ports while the appliance is in use. The appliance may force the mouth and airway into an unnaturally open position without requiring the lower jaw to be displaced forward. A tongue rest may extend through the device to support the tongue, while simultaneously providing slight upward pressure on the tongue to further open the airway.

4 Claims, 6 Drawing Sheets

(56) References Cited

U.S. PATENT DOCUMENTS

| | | | | |
|---|---|---|---|---|
| 8,387,620 B1* | 3/2013 | Vaska | ................... | A61F 5/566 |
| | | | | 128/848 |
| 8,752,555 B2* | 6/2014 | Goldsby | ................ | A61B 1/24 |
| | | | | 128/857 |
| 2006/0084024 A1* | 4/2006 | Farrell | ................... | A61C 7/08 |
| | | | | 433/6 |
| 2011/0220124 A1* | 9/2011 | Vaska | ................... | A61F 5/566 |
| | | | | 128/848 |

* cited by examiner

OBSTRUCTIVE SLEEP APNEA AND SNORING PREVENTION DENTAL APPLIANCE

RELATED APPLICATION

This application claims priority to provisional patent application U.S. Ser. No. 62/099,284 filed on Jan. 2, 2015, the entire contents of which is herein incorporated by reference.

BACKGROUND

The embodiments herein relate generally to dental appliances, and more particularly, to a dental appliance configured to prevent or reduce obstructive sleep apnea and snoring.

Most oral appliances for treating sleep apnea and snoring are designed to move the lower jaw forward and sometimes combined with tongue suppression, opening the airway and helping with the problem. However, moving the lower jaw forward and using tongue suppression is very uncomfortable and causes many side effects.

Therefore, what is needed is a dental appliance that is configured to treat obstructive sleep apnea and snoring without requiring the lower jaw to be moved forward or tongue suppression to open the airway.

SUMMARY

Some embodiments of the present disclosure include a dental appliance for treating/preventing sleep apnea and snoring. The dental appliance may be a wedge-shaped device designed to be positioned between the lower and upper jaw, wherein the device is thicker within a front area of the mouth and thinner within a back area of the mouth. The device may include upper and lower teeth channels to accommodate the teeth and a plurality of breathing ports positioned between the upper and lower teeth channels, the breathing ports being configured to allow a user to breathe through the ports while the appliance is in use. The appliance may force the mouth and airway into an unnaturally open position without requiring the lower jaw to be displaced forward or the use of tongue suppression. A tongue rest may extend through the device to support the front portion of the tongue, while simultaneously providing slight upward pressure on the tongue to further open the airway.

BRIEF DESCRIPTION OF THE FIGURES

The detailed description of some embodiments of the invention is made below with reference to the accompanying figures, wherein like numerals represent corresponding parts of the figures.

DETAILED DESCRIPTION OF CERTAIN EMBODIMENTS

Figure 1:
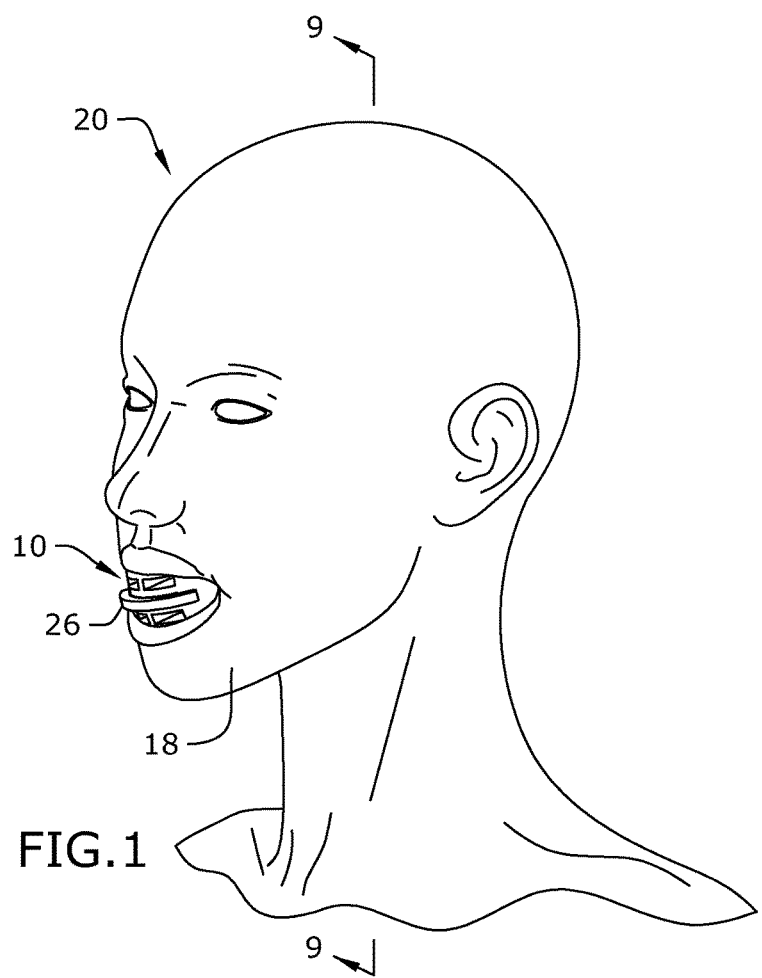
FIG. 1 is a perspective view of one embodiment of the present disclosure, shown in use.
Figure 2:
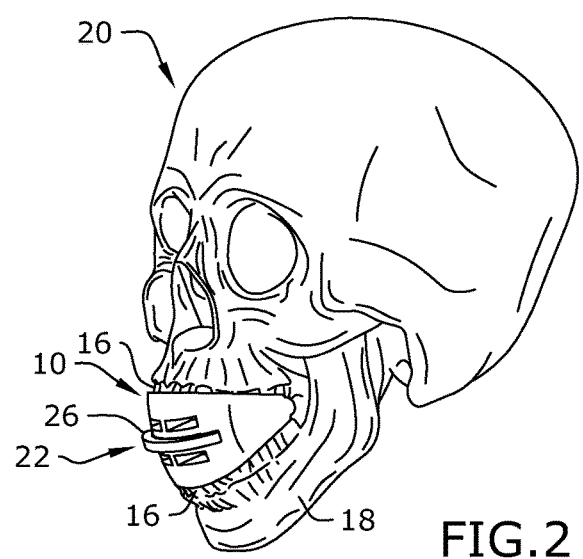
FIG. 2 is a perspective view of one embodiment of the present disclosure, shown in use.
Figure 3:
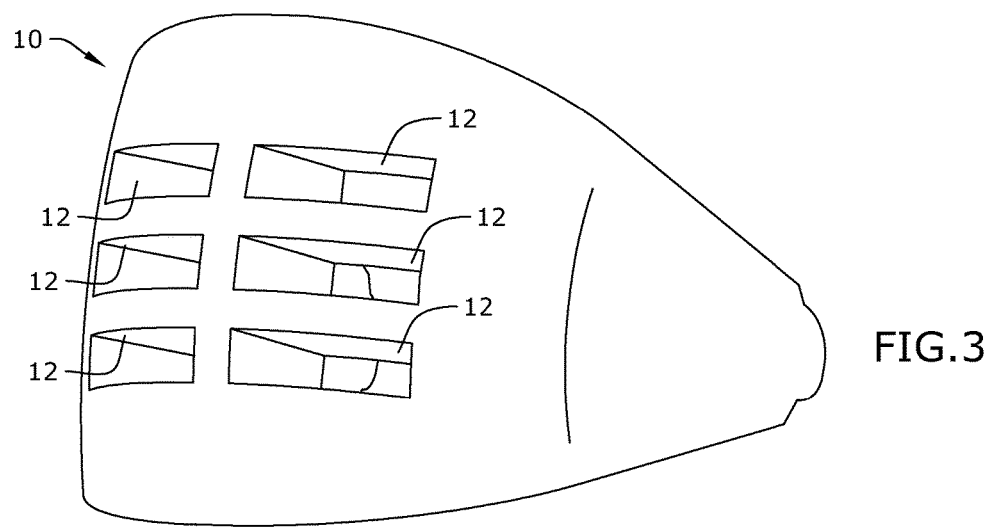
FIG. 3 is a front perspective view of one embodiment of the present disclosure.
Figure 4:
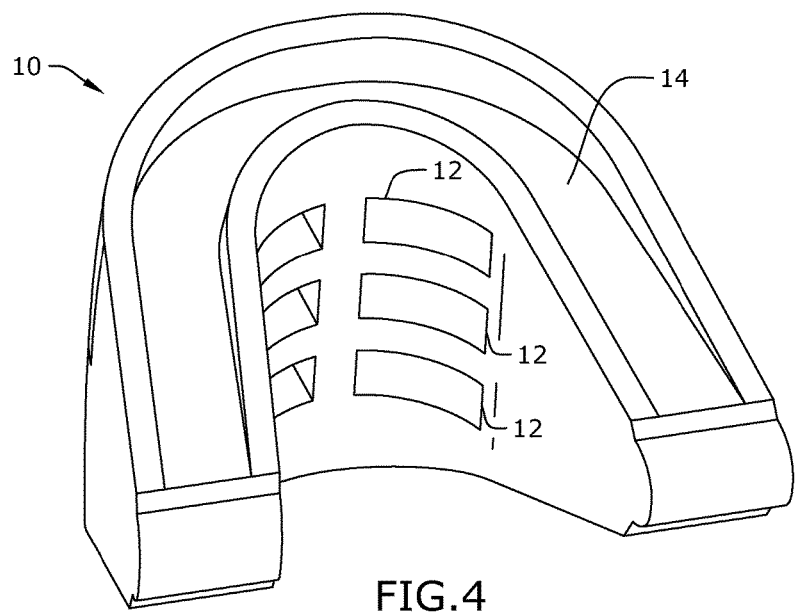
FIG. 4 is a rear perspective view of one embodiment of the present disclosure.

In the following detailed description of the invention, numerous details, examples, and embodiments of the invention are described. However, it will be clear and apparent to one skilled in the art that the invention is not limited to the embodiments set forth and that the invention can be adapted for any of several applications.

The device of the present disclosure may be used to treat and/or prevent obstructive sleep apnea and snoring and may comprise the following elements. This list of possible constituent elements is intended to be exemplary only, and it is not intended that this list be used to limit the device of the present application to just these elements. Persons having ordinary skill in the art relevant to the present disclosure may understand there to be equivalent elements that may be substituted within the present disclosure without changing the essential function or operation of the device.

1. Dental Appliance
2. Breathing Ports
3. Teeth Channels
4. Tongue Rest

The various elements of the dental appliance for treating and/or preventing obstructive sleep apnea and snoring of the present disclosure may be related in the following exemplary fashion. It is not intended to limit the scope or nature of the relationships between the various elements and the following examples are presented as illustrative examples only.

By way of example, and referring to FIGS. 1-11, some embodiments of the dental appliance 10 of the present disclosure comprise a dental appliance 10 configured to fit between the lower and upper jaw 18 of a user 20, the dental appliance 10 comprising teeth channels 14 configured to accommodate a user's teeth 16 and a plurality of breathing ports 12 configured to allow a user 20 to breathe through the ports 12 while the appliance 10 is in the user's mouth. The teeth channels 14 may comprise various angles and surface textures along with raised outer edges to prevent a user's teeth 16 from slipping out of the channels 14 during use. As shown in FIGS. 4, 6-8, and 11 the appliance 10 of the present disclosure may be substantially U-shaped and may closely approximate the shape of a user's jaw 18. Additionally, the appliance 10 may be substantially wedge-shaped, such that the appliance 10 is thicker at a region configured to be positioned within the front of a user's mouth and thinner at a region configured to be positioned within the back of a user's mouth. Because of the structure of the appliance 10, the appliance 10 may hold the user's 20 mouth in an unnatural open position. Specifically, the appliance 10 may cause the user's 20 mouth and airway 28 to be opened without the mandible, or lower jaw 18, being required to move forward, wherein forward movement is defined as movement away from a user's throat.

As shown in FIGS. 1, 2, 4, and 9, the appliance 10 may comprise a tooth channel 14 on both an upper surface and a lower surface thereof, such that the user's upper and lower teeth 16 may be accommodated therein, wherein the breathing ports 12 may be positioned between the upper and lower tooth channel 14 proximate to a portion configured to be positioned within the front of a user's mouth. In some embodiments, the appliance 10 comprises a plurality of breathing ports 12 equally spaced about the front of the appliance 10. For example, the appliance 10 may comprise about 6 breathing ports 12, such as two columns of three breathing ports 12. The breathing ports 12 may be substantially rectangular in shape and may extend through an entire width of the appliance 10.

Figure 5:
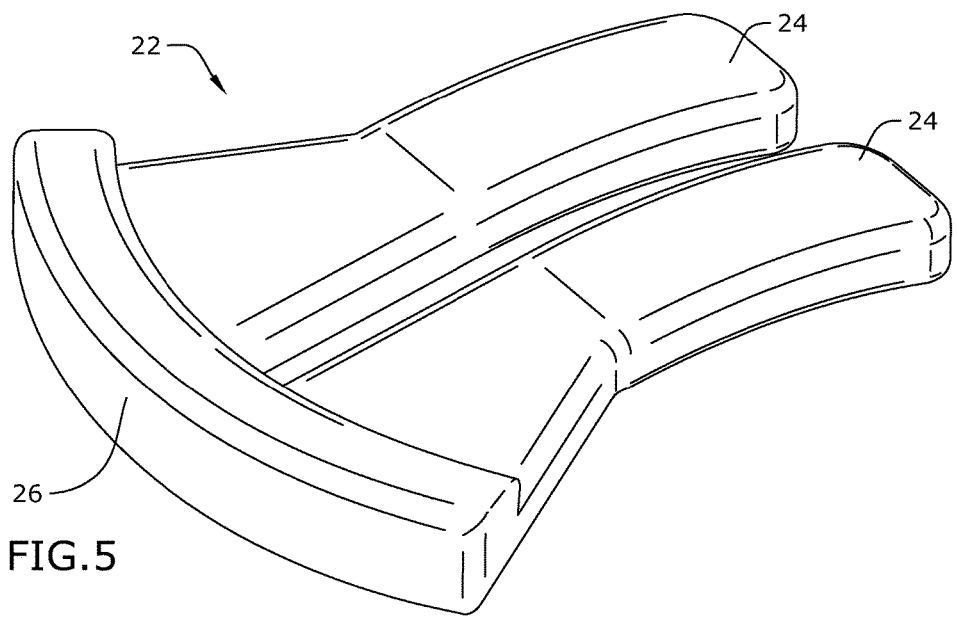
FIG. 5 is a perspective view of one embodiment of the present disclosure.
Figure 6:
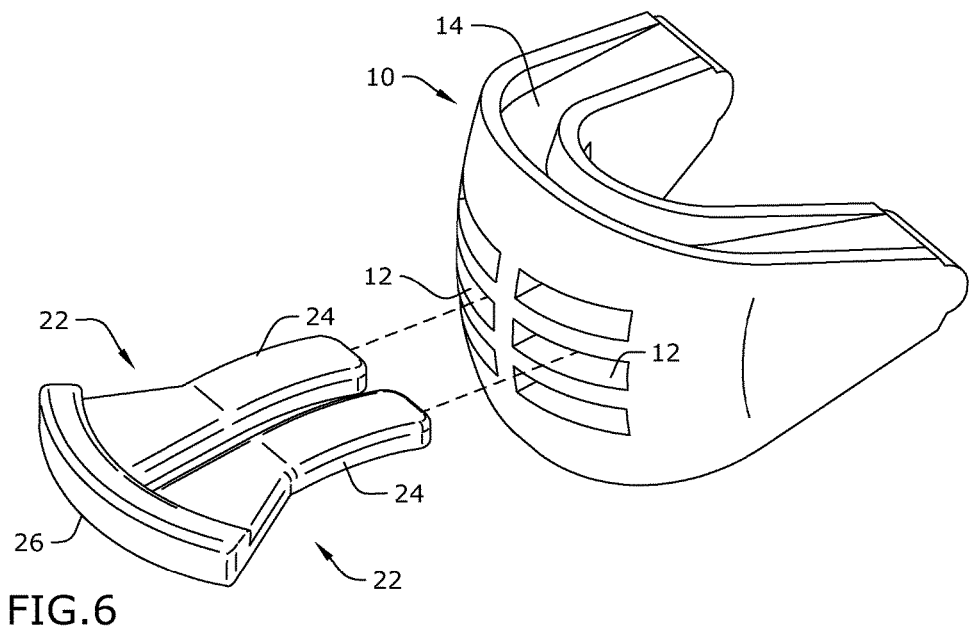
FIG. 6 is an exploded view of one embodiment of the present disclosure.
Figure 7:
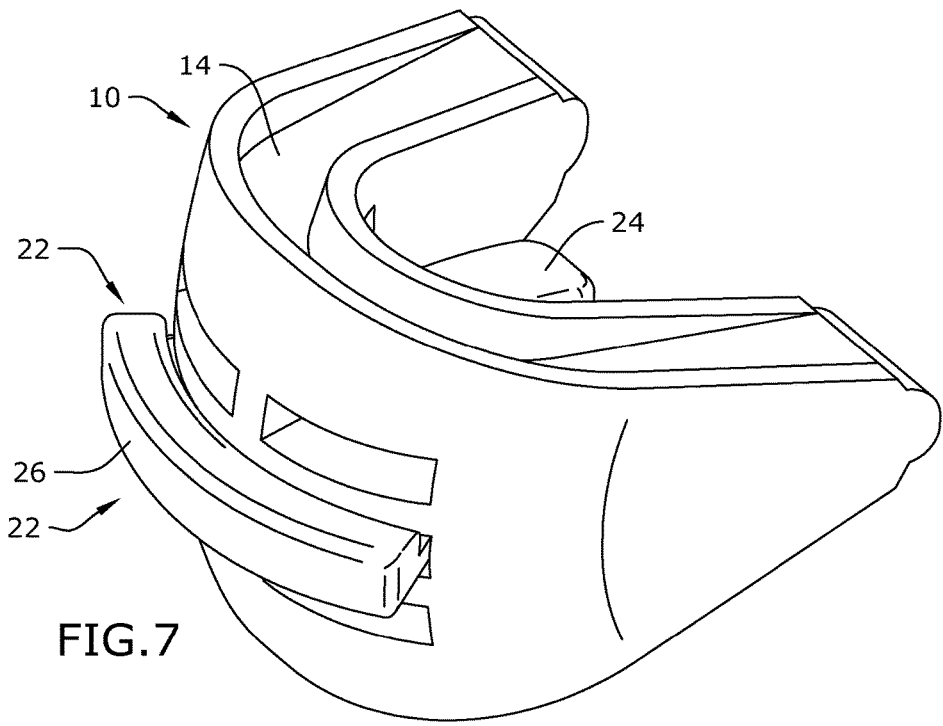
FIG. 7 is a perspective view of one embodiment of the present disclosure.
Figure 8:
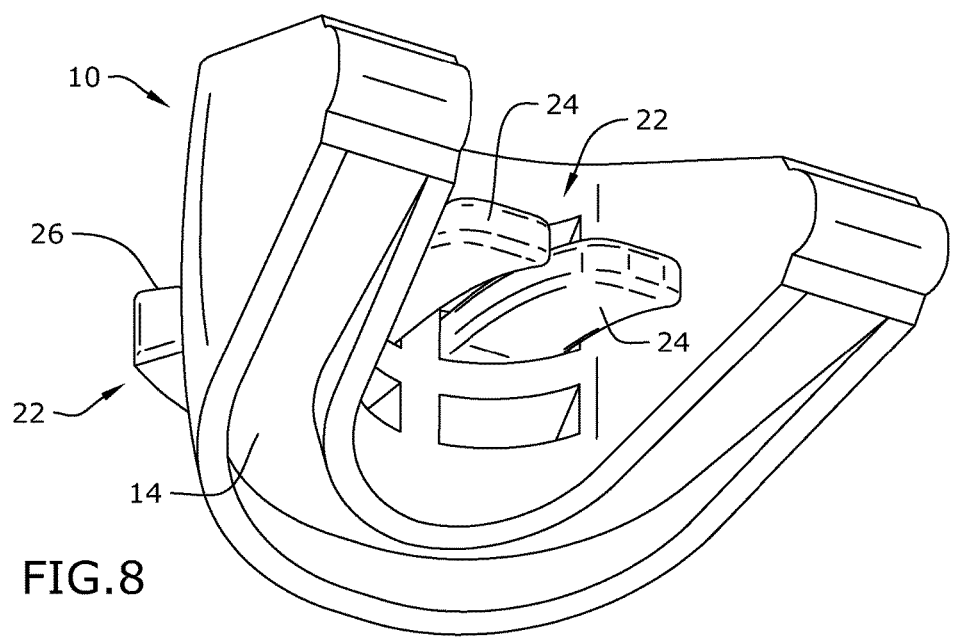
FIG. 8 is a lower perspective view of one embodiment of the present disclosure.
Figure 9:
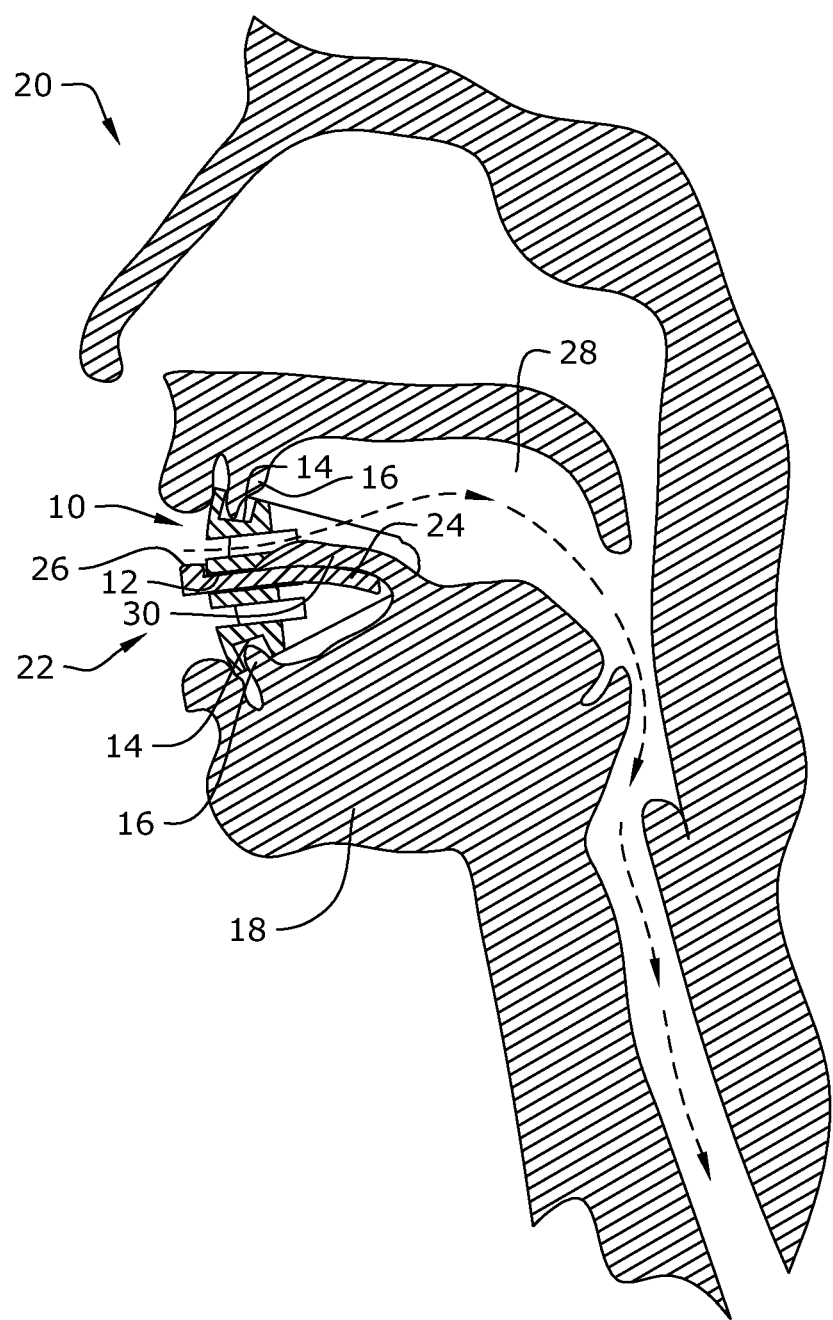
FIG. 9 is a section detail view of one embodiment of the present disclosure, taken along line 9-9 in FIG. 1.
Figure 10:
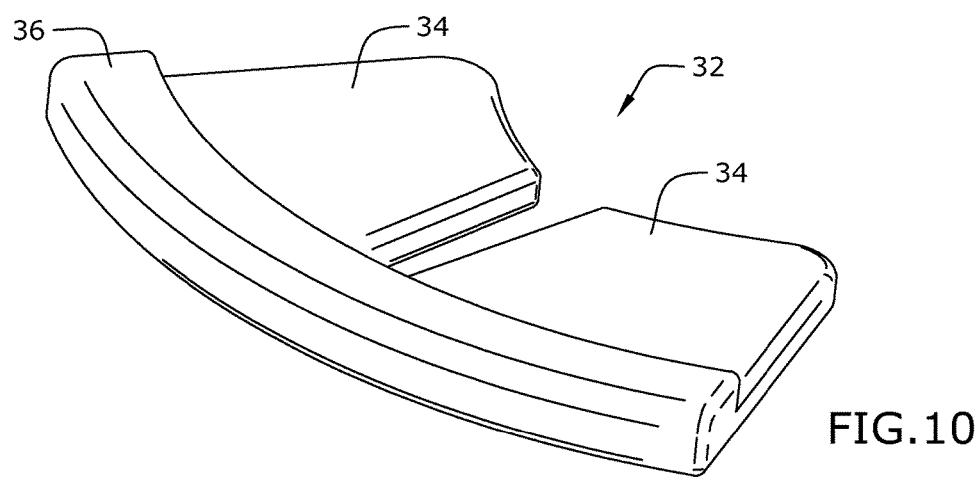
FIG. 10 is a perspective view of one embodiment of the present disclosure.

As shown in FIG. 5-9, some embodiments of the appliance 10 may further comprise a tongue rest 22 configured to engage with at least one breathing port 12, wherein the tongue rest 22 comprises at least one tongue rest stem 24 extending from a tongue rest handle 26. The tongue rest stem 24 may at least partially extend through the breathing port 12, wherein the tongue rest stem 24 is configured to support at least the front portion of a user's tongue 30, as shown in FIG. 1. Specifically, the tongue rest 22 may provide a slight, upward pressure on the tongue 30, helping to further open the user's airway 28. The tongue rest handle 26 may provide the user 20 with a means of inserting the tongue rest 22 into the breathing port 12 while simultaneously stopping the tongue rest 22 at various lengths from being pushed completely through the breathing port 12. In some embodiments, the tongue rest 22 comprises a pair of tongue rest stems 24 configured to extend through a pair of breathing ports 12, wherein the handle 26 prevents the tongue rest 22 from passing entirely through the breathing ports 12. As shown in the figures, the tongue rest stems 24 may curve downward toward the bottom of a user's mouth lifting the tongue 30 higher than it would fall naturally, which may change the muscle tone and open the airway 28 more than conventional devices. The tongue rest stems 24 may also be wider proximate to the handle 26 and narrower distal from the handle 26, as shown in FIG. 5.

Figure 11:
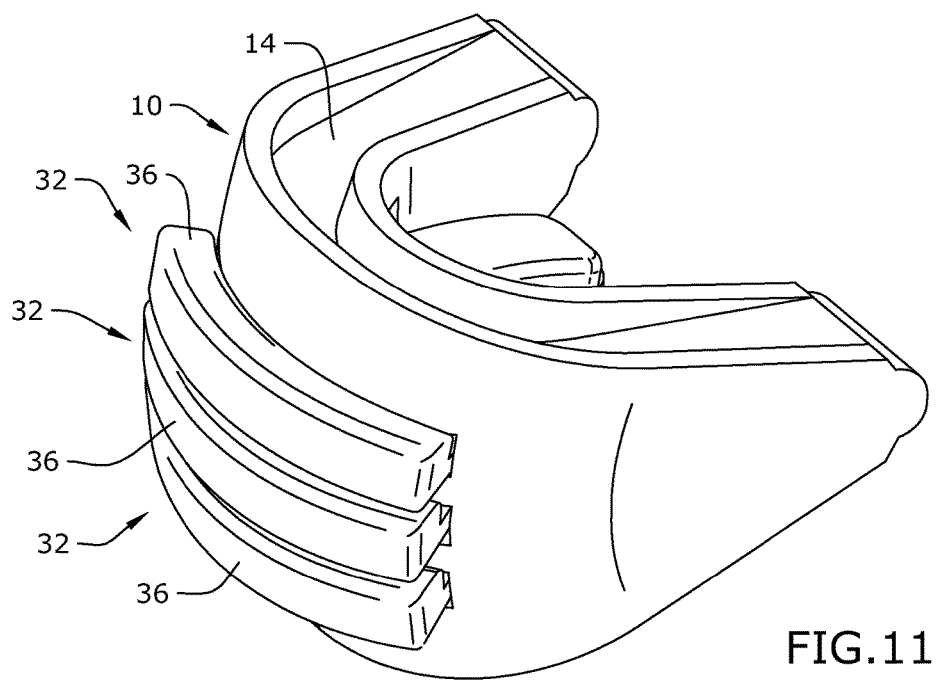
FIG. 11 is a perspective view of one embodiment of the present disclosure.

Alternatively, some embodiments of the appliance 10 may further comprise an airway blocker 32 configured to block airflow through the breathing ports 12, wherein the airway blocker 32 comprises an airway blocker arm 34 extending from an airway blocker handle 36 and wherein the airway blocker handle 36 is configured to completely block the breathing ports 12 while simultaneously preventing the airway blocker 32 from slipping through the breathing port 12. In embodiments, such as that shown in FIG. 10, the airway blocker 32 may comprise a pair of airway blocker arms 34 which may be shorter and differently shaped than the tongue rest stems 24. As shown in FIG. 11, a user may use multiple airway blockers 32 to block all of the breathing ports 12, resulting in the user's mouth being held open, but preventing the user 20 from breathing through the mouth, and forcing the user 20 to breathe through his or her nose. In other embodiments, the airway blocker 32 may also be configured to prevent the breathing ports 12 from collapsing during the teeth molding process. After the molding process is completed, the airway blockers 32 may be removed and stored in case the molding process has to be repeated.

The appliance 10 of the present disclosure may fit within a user's mouth similar to a boxing or sports appliance, wherein the shape is designed to open the jaw, enlarging the opening in the throat providing for easy airflow. The breathing ports may also provide a mechanism for non-restricted air flow.

To use the appliance of the present disclosure, a user may determine which size appliance is required and place the appliance 10 in boiling water for about 10 seconds, dipping the appliance in cool water for 2 seconds, and then placing the appliance in the user's mouth to mold the appliance to a user's teeth and jaws. If a softer gel-type material is used, the boil and bite process may not be necessary to mold the appliance 10 to the user's mouth/teeth. Before the user goes to sleep, he or she may place the appliance in her mouth, opening the airway more effectively than traditional oral devices that move the lower jaw forward. The created larger airway may allow the muscles to relax normally, avoiding snoring and the symptoms of sleep apnea.

The appliance 10 of the present disclosure may be made using any suitable material and, in some embodiments, comprises a rubber or rubber-like material. For example, the appliance 10 may be made using an injection rubber mold. Moreover, the rubber may be fitted or molded around the upper and lower teeth 16 for a custom fit. For example, the appliance 10 may be heated and then molded. The appliance 10 may be made in a variety of sizes depending on the needs of the user. Different sizes may also be dependent on the gender and age of the individual using the appliance 10.

Compared to conventional devices for treating sleep apnea, the device of the present invention does not move the mandible (or lower jaw) forward or the need for tongue suppression, which causes discomfort in the user. Rather, the device of the present invention opens the mouth to sufficiently open the airway, while simultaneously providing breathing ports such that a user can breathe through his or her mouth. In contrast, most conventional devices require a user to breathe through his or her nose.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A device for treating sleep apnea and snoring, the device comprising:
   a dental appliance configured to fit between a lower jaw and an upper jaw of a user, the dental appliance comprising:
      teeth channels configured to accommodate a user's teeth; and
      a plurality of breathing ports configured to allow a user to breathe through the breathing ports while the appliance is in the user's mouth; and
      a tongue rest configured to extend through the dental appliance and support a user's tongue,
   wherein:
      the appliance is U-shaped and closely approximates a shape of the user's jaws;
      the appliance is wedge-shaped, such that the appliance is thicker at a region configured to be positioned within a front area of the user's mouth and thinner at a region configured to be positioned within a back of the user's mouth;
      the tongue rest comprises a pair of tongue rest stems extending from a tongue rest handle, the tongue rest stems being configured to extend through a pair of adjacent breathing ports;
      the tongue rest stems are configured to be positioned under a portion of the user's tongue, applying upward pressure on the user's tongue; and the appliance comprises six breathing ports, the breathing ports being arranged in two equal columns.

2. The device of claim 1, wherein the teeth channels comprise raised outer edges to prevent the teeth from slipping out of the teeth channels during use.

3. A device for treating sleep apnea and snoring, the device comprising:

a dental appliance configured to fit between a lower jaw and an upper jaw of a user, the dental appliance comprising:
- a wedge-shaped device, wherein the wedge-shaped device is thicker at a region configured to be positioned within a front area of the user's mouth and thinner at a region configured to be positioned within a back of the user's mouth;
- an upper teeth channel positioned on an upper surface of the wedge-shaped device, the upper teeth channel configured to accommodate a user's upper teeth;
- a lower teeth channel positioned on a lower surface of the wedge-shaped device, the lower teeth channel configured to accommodate a user's lower teeth;
- a plurality of breathing ports positioned between the upper teeth channel and the lower teeth channel, the plurality of breathing ports being configured to allow a user to breathe through the ports while the appliance is in the user's mouth; and
- a tongue rest configured to extend through the dental appliance and support a user's tongue, wherein:
- the appliance forces the user's mouth and airway into an unnaturally open position without requiring the lower jaw to be displaced forward;
- the tongue rest comprises a pair of tongue rest stems extending from a tongue rest handle, the tongue rest stems being configured to extend through a pair of adjacent breathing ports;
- the tongue rest stems are configured to be positioned under a portion of the user's tongue, applying upward pressure on the user's tongue; and
- the plurality of breathing ports comprises six breathing ports, the breathing ports being arranged in two equal columns.

4. The device of claim 3, wherein the appliance is U-shaped and closely approximates a shape of the user's jaws.

* * * * *